(12) United States Patent
Ford (10) Patent No.: US 8,377,397 B2
(45) Date of Patent: Feb. 19, 2013

(54) COMBUSTION TUBE

(75) Inventor: Gordon C. Ford, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 0 days.

(21) Appl. No.: 13/223,589

(22) Filed: Sep. 1, 2011

(65) Prior Publication Data

US 2012/0225000 A1 Sep. 6, 2012

Related U.S. Application Data

(60) Provisional application No. 61/448,400, filed on Mar. 2, 2011.

(51) Int. Cl.
*B01L 3/14* (2006.01)
*G01N 31/12* (2006.01)

(52) U.S. Cl. .......................... 422/549; 422/78

(58) Field of Classification Search .................... 422/549
See application file for complete search history.

(56) References Cited

U.S. PATENT DOCUMENTS

| | | | |
|---|---|---|---|
| 2,809,100 A | 10/1957 | Krasl | |
| 3,923,464 A * | 12/1975 | Sitek et al. | ...................... 422/78 |
| 4,234,541 A | 11/1980 | Bredeweg et al. | |
| 6,270,728 B1 * | 8/2001 | Wijnschenk et al. | ......... 422/549 |
| 2011/0075696 A1 | 3/2011 | Ford | |

OTHER PUBLICATIONS

U.S. Appl. No. 13/198,746, filed Aug. 5, 2011 entitled "Combustion Furnace Auto Cleaner".

* cited by examiner

*Primary Examiner* — Jill Warden
*Assistant Examiner* — Julie Tavares
(74) *Attorney, Agent, or Firm* — Price Heneveld LLP (57) ABSTRACT

A combustion tube comprises a generally cylindrical body with an outwardly extending annular tube stop spaced from one end of the combustion tube for engaging a combustion tube mounting assembly and fixing the tube in a precise position. Near the opposite end of the tube is an enlarged opening for receiving an upper seal assembly of a combustion furnace with the outer annular shoulder of the upper end of the tube having a rolled edge to facilitate the insertion of the tube through the seal in the upper seal assembly of the furnace. The combustion tube is made of quartz glass to withstand the temperatures encountered in the furnace. The combustion tube is specifically designed and adapted to be precisely positioned in an induction furnace with an easy tube removal system for the furnace.

17 Claims, 10 Drawing Sheets

COMBUSTION TUBE

CROSS-REFERENCE TO RELATED APPLICATIONS

This application claims priority under 35 U.S.C. §119(e) and the benefit of U.S. Provisional Application No. 61/448,400 entitled COMBUSTION TUBE, filed on Mar. 2, 2011, by Gordon C. Ford.

BACKGROUND OF THE INVENTION

The present invention relates to a combustion tube for an induction furnace employed in an analytical instrument.

Quartz combustion tubes have been used in connection with combustion furnaces for many years for enclosing a sample for the analysis of elements, such as carbon or sulfur. One commercially available analyzer is Model No. CS600, available from Leco Corporation of St. Joseph, Mich. Such an analyzer uses a quartz combustion tube which is typically used to maintain a pressurized oxygen-rich environment for the combustion of a sample in a ceramic crucible held within an induction coil surrounding the combustion tube. U.S. Pat. Nos. 2,809,100, 3,923,464, and 4,234,541 are examples of systems employing such quartz combustion tubes. The disclosures of these patents are incorporated herein by reference.

During the combustion process, byproducts of combustion frequently cause deposits on the combustion tube. The quartz tube must be cleaned and eventually replaced to maintain the accuracy of sample results. The mounting of a combustion tube in existing furnaces equipped with an auto cleaner is both time consuming and cumbersome, requiring that fluid fittings and electrical connections be removed and the auto-cleaner device removed from the combustion tube area of the furnace. The combustion tube is removed from the top of the furnace housing once the disassembly has been completed. Once a new combustion tube has been installed, the furnace has to be reassembled, frequently including the connection of fluid couplings which can lead to leaks in the system if not properly accomplished. Thus, the maintenance, removal and replacement of combustion tubes in existing furnaces is difficult, time consuming, and leads to downtime for the operation of an analyzer.

Accordingly, there exists a need for an improved combustion tube for use in an analytical combustion furnace which can be readily accessed without disconnecting fluid fittings, auto-cleaners, or the like from the furnace assembly.

SUMMARY OF THE INVENTION

The system of the present invention accomplishes this goal by providing an improved combustion tube which cooperates with a mounting system for the combustion tube. The combustion tube is removably installed through an aperture in the floor of a furnace housing and can be manually or automatically unlocked from the floor of the furnace housing by a cam-locking mechanism for positioning the combustion tube in an open area of the furnace below the furnace housing for easy removal and replacement.

In a preferred embodiment, a combustion tube includes a generally cylindrical body with an annular outwardly extending ring for releasably engaging a mounting assembly. The mounting assembly includes a base seal assembly which is placed on a lower seal assembly of a combustion furnace and is raised to automatically align with the upper furnace seal. Cams in the floor of the furnace housing engage a cam associated with the base seal assembly to lock the combustion tube in place as it is raised into the furnace housing. As a result of this construction, a downwardly removable combustion tube is provided, and the steps of disassembling the furnace components, including the self-cleaning mechanism located above the combustion tube, is eliminated as is the necessity for skilled technicians to replace the combustion tube. An operator can readily unlock the combustion tube from the furnace and lower it for access and replacement.

These and other features, objects and advantages of the present invention will become apparent upon reading the following description thereof together with reference to the accompanying drawings.

DETAILED DESCRIPTION OF THE PREFERRED EMBODIMENT

Figure 1:
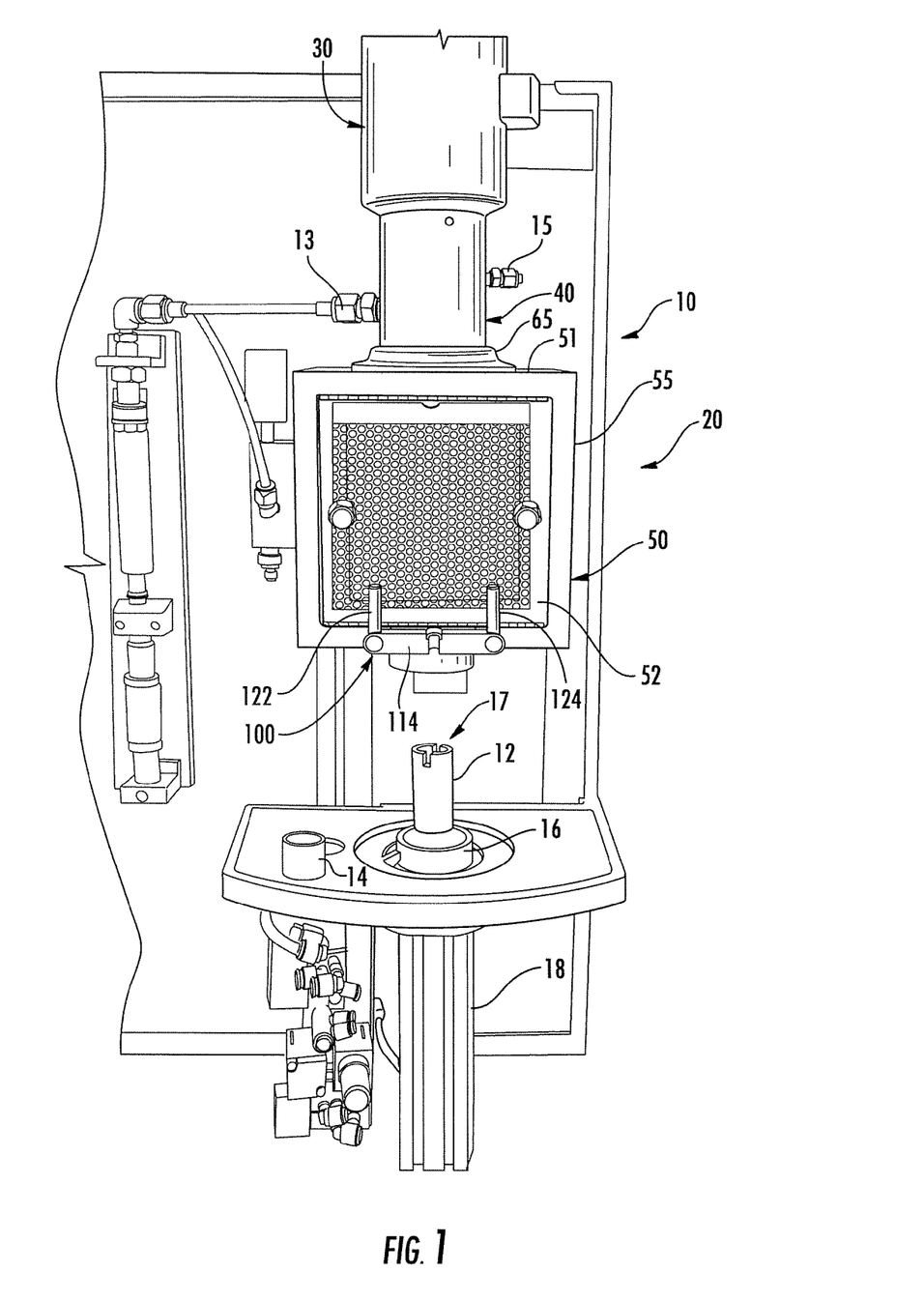
FIG. 1 is a fragmentary front perspective view of a combustion furnace embodying the present invention.
Figure 2:
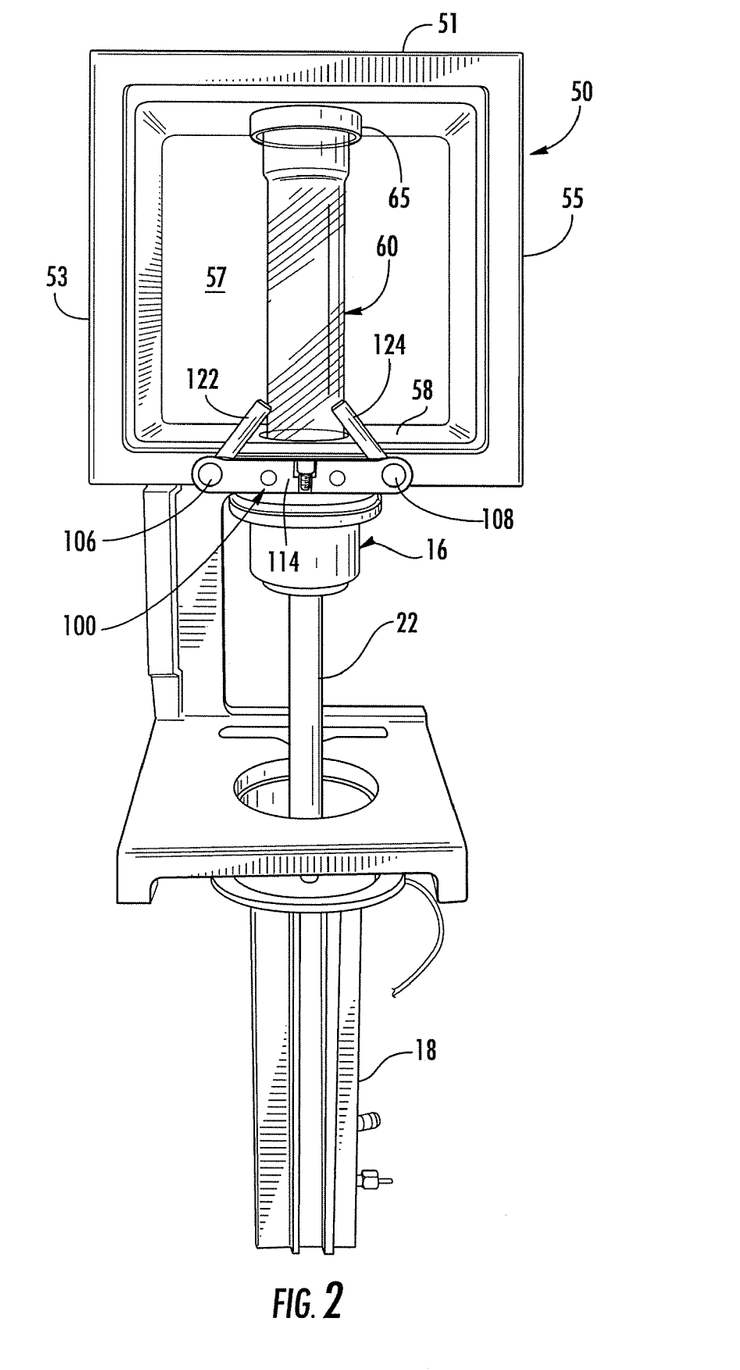
FIG. 2 is a front perspective view of the furnace housing with the cover removed showing the combustion tube and locking mechanism for the tube, shown in an unlocked position.
Figure 3:
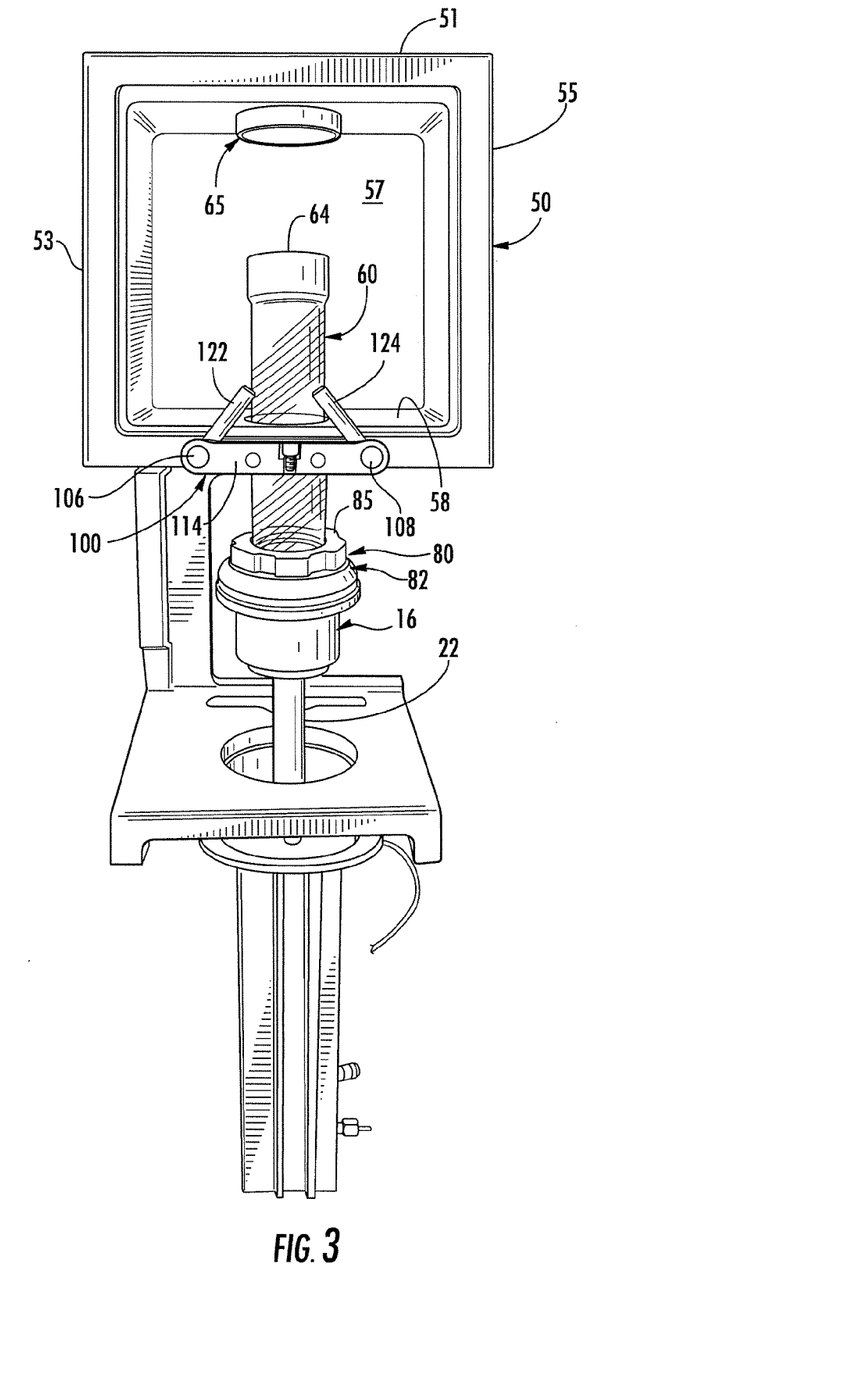
FIG. 3 is a front perspective view of the furnace shown in FIG. 2, showing the lowering and raising of the combustion tube through an aperture in the furnace housing floor.
Figure 4:
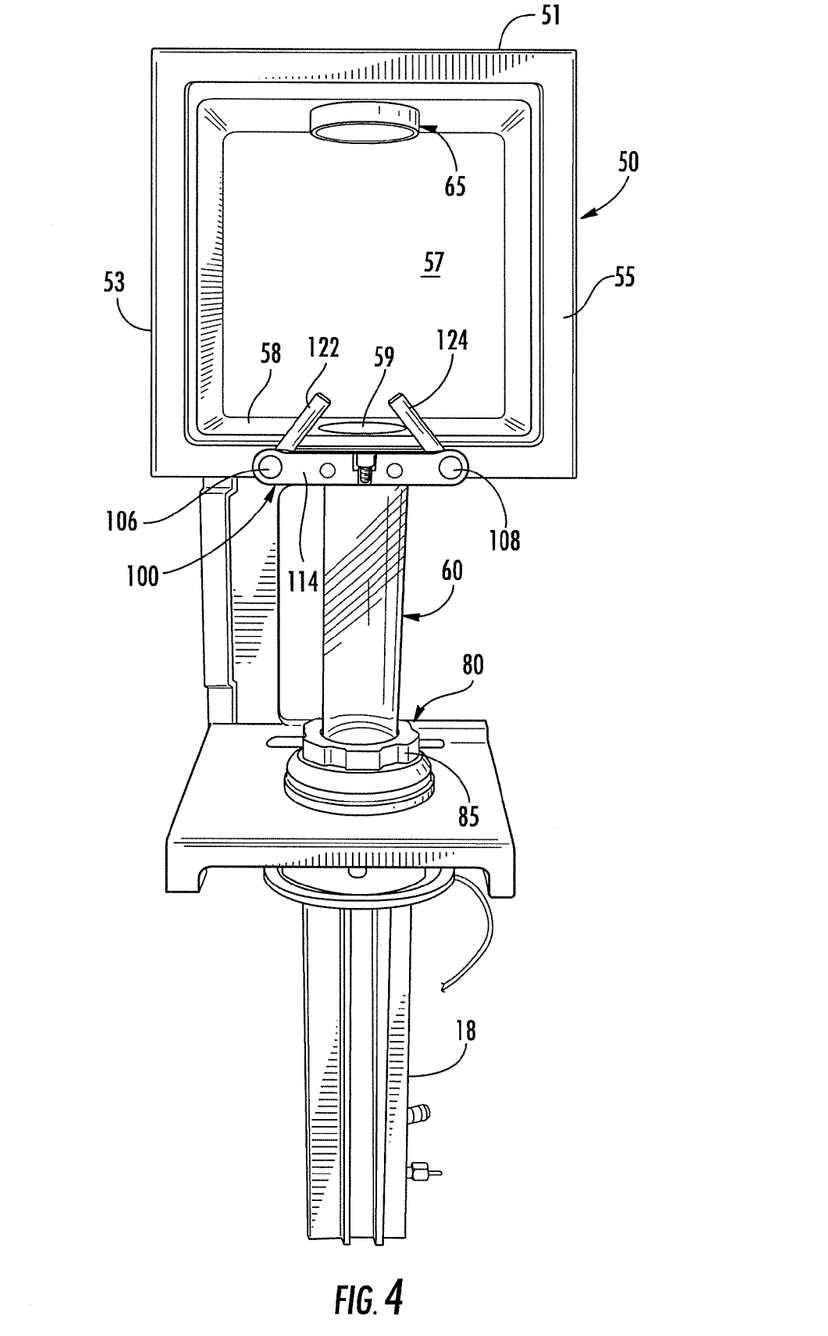
FIG. 4 is a front perspective view of the furnace shown in FIG. 3, showing the combustion tube lowered from the furnace housing in a position for removal/replacement.
Figure 5:
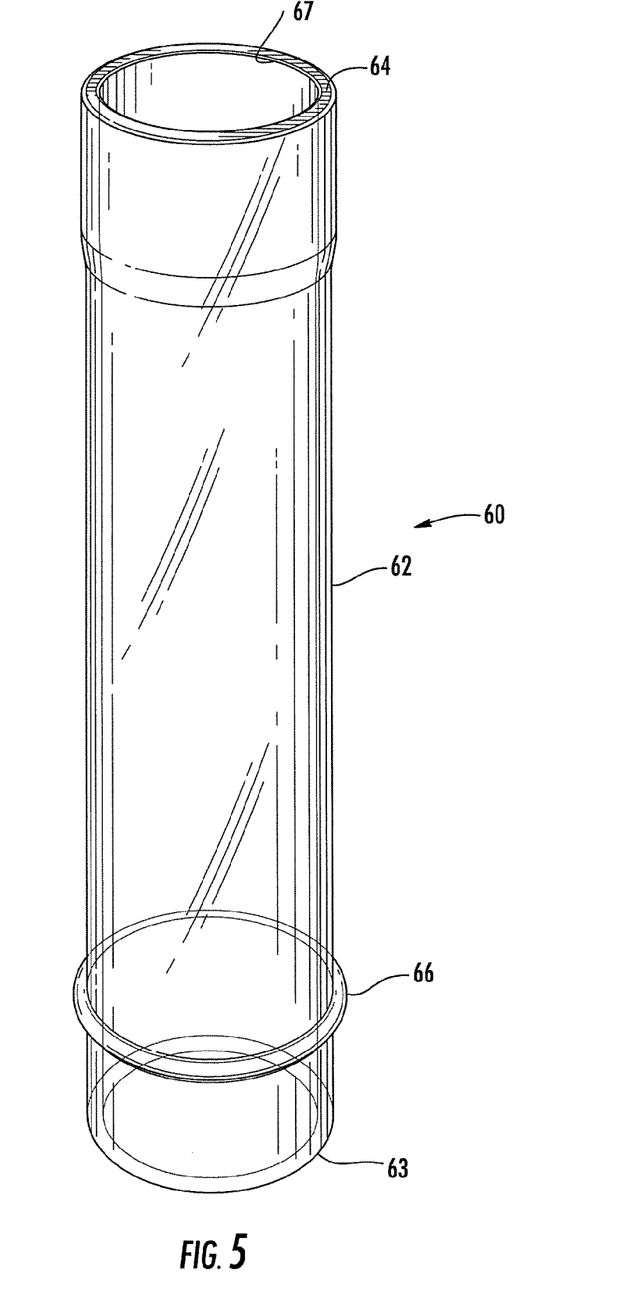
FIG. 5 is a perspective view of the improved combustion tube.

Referring initially to FIG. 1, there is shown an analyzer 10 which includes an induction furnace assembly 20, including the auto cleaning mechanism 30 described in detail in U.S. patent application Ser. No. 13/198,746, filed Aug. 5, 2011, entitled COMBUSTION FURNACE AUTO CLEANER, the disclosure of which is incorporated herein by reference. The analyzer components themselves can be similar to those employed in a carbon sulfur analyzer, Model No. CS600, available from Leco Corporation of St. Joseph, Mich. The analyzer 10 is shown in FIG. 1 with the cover shrouds removed to expose the components of the induction furnace, which are also shown in FIGS. 2-4. The detachable auto cleaner assembly 30 is removably mounted by a bayonet connection to a heated filter assembly 40, which is sealably secured at 65 to the top wall 51 of combustion housing 50. Housing 50 additionally includes side walls 53 and 55, an interface back wall 57, and floor 58.

The housing 50 is mounted to structural base 17 of the analyzer 10, which includes housing 50. The front of furnace housing 50 is enclosed by a quickly removable door 52, which, when removed as seen in FIG. 2, exposes the combustion tube 60 of the present invention (FIGS. 5-10). An induction coil (not shown) surrounds the combustion tube to heat an analytical specimen held in a ceramic crucible 14 (FIG. 1) when introduced into the hot zone of combustion tube 60 by vertically movable pedestal 12. Tube 60 is sealably coupled to the lower end of filter assembly 40 by an upper seal assembly 65. The pedestal 12 (FIG. 1) for holding a sample-holding crucible 14 is positioned on a cup-shaped lower seal assembly 16 and is raised and lowered into combustion tube 60 by means of a pneumatic cylinder 18 and cylinder rod 22 (FIG. 3) coupled to assembly 16. In the position shown in FIG. 1, the cylinder rod 22 is in a lowered retracted position within cylinder 18.

A combustion tube base assembly 80 (FIGS. 3, 4, 11, and 12) sealably couples the lower end 63 of tube 60 to the pedestal's lower seal assembly 16 such that, during combustion of a sample, oxygen flows upwardly through a gas inlet in assembly 16 to sweep byproducts of combustion into gas outlet 13 (FIG. 1) for analysis. Oxygen is also supplied to the upper end of combustion tube 60 by an oxygen inlet 15 and suitable passageways to an inlet lance to direct oxygen into crucible 14 during combustion. Housing 50 includes cam-actuated locking assembly 100 (FIG. 2) which cooperates with base assembly 80 to allow the combustion tube 60 to be easily withdrawn from underneath the floor of combustion housing 50. Assembly 100 includes arms 122, 124 on pivoted cams 106, 108 mounted to housing 50 by a mounting plate 114, as described in detail in U.S. patent application Ser. No. 12/889,628 filed on Sep. 24, 2010, entitled EASILY REMOVABLE COMBUSTION TUBE, the disclosure of which is incorporated herein by reference.

Figure 6:
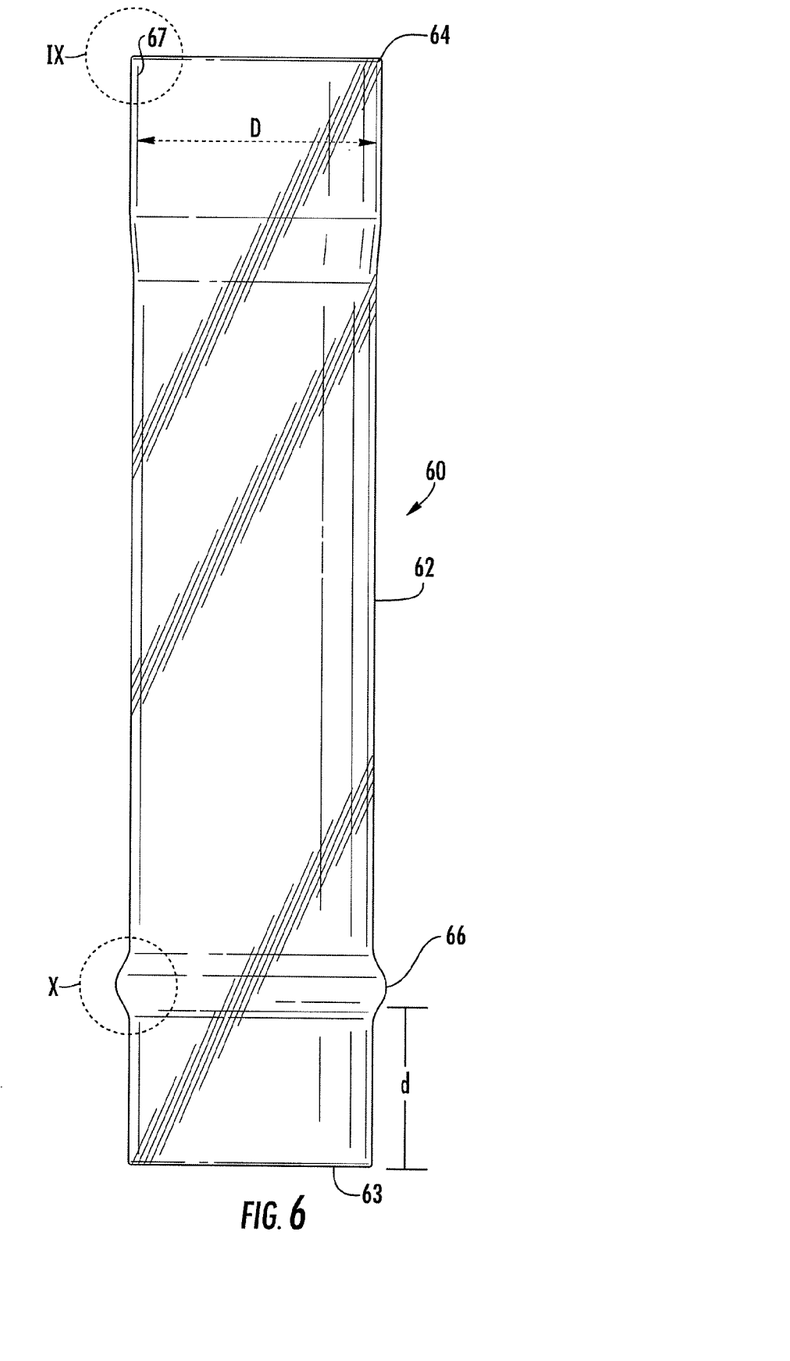
FIG. 6 is a front elevational view of the combustion tube.
Figure 7:
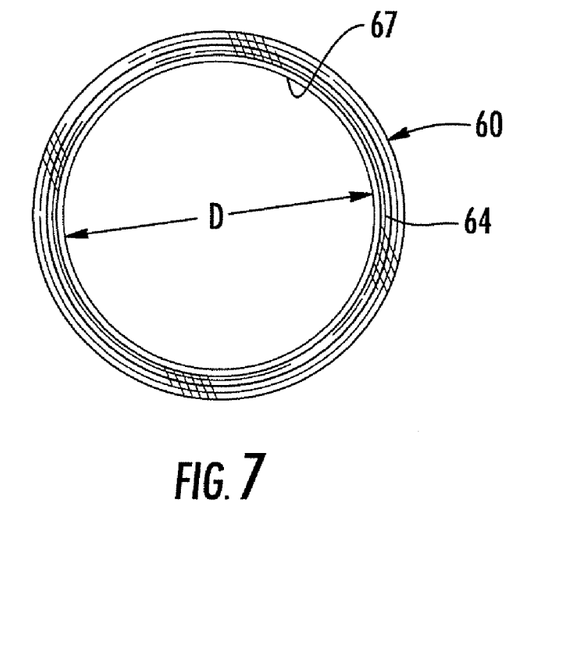
FIG. 7 is a top plan view of the combustion tube.
Figure 8:
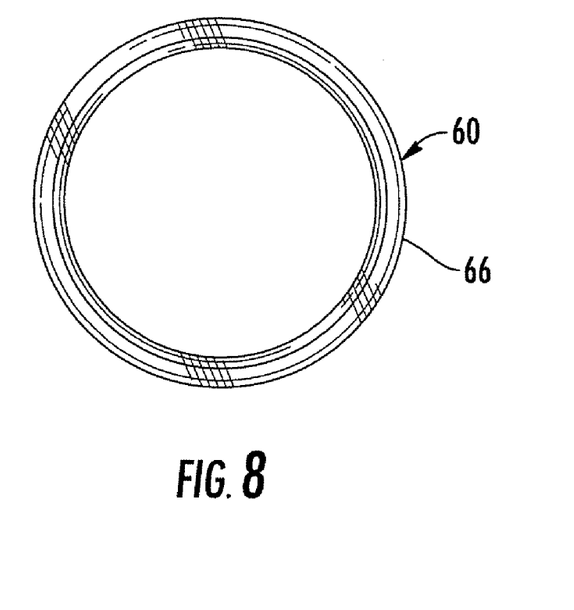
FIG. 8 is a bottom plan view of the combustion tube.

Referring to FIGS. 5-11, there is shown a combustion tube 60, which has a generally cylindrical body 62, including a first or lower end 63 and a second or upper end 64. Spaced from the lower end a predetermined distance "d" (shown in FIG. 6) is a tube stop or stop collar 66 comprising an annular ring or shoulder formed in and integral with the cylindrical body 62 of the combustion tube 60. The opposite end 64 of the tube is enlarged to provide a somewhat larger diameter "D", as seen in FIGS. 6 and 7, such that the open mouth 67 of the upper end 64 of tube 60 mates with an internal O-ring in the upper seal assembly 65 (FIGS. 2-4) of the combustion furnace 20. Surrounding the annular upper end 64 of the combustion tube 60 is a rolled edge 68 (FIG. 9) which provides a rounded interface between the upper end of tube 60 as it engages the seal of the upper seal assembly 65, as illustrated in FIG. 2.

An upper seal assembly 65 includes an internal O-ring seal on a collar that engages the inner cylindrical surface of the mouth 67 at the upper end 64 of combustion tube 60. The furnace 20 also includes a base assembly 80, shown in detail in FIGS. 12-15, which receives the lower end 63 of combustion tube 60 with tube stop 66 indexing the position of the tube with respect to the lower base assembly 80.

Figures 9, 10, 11:
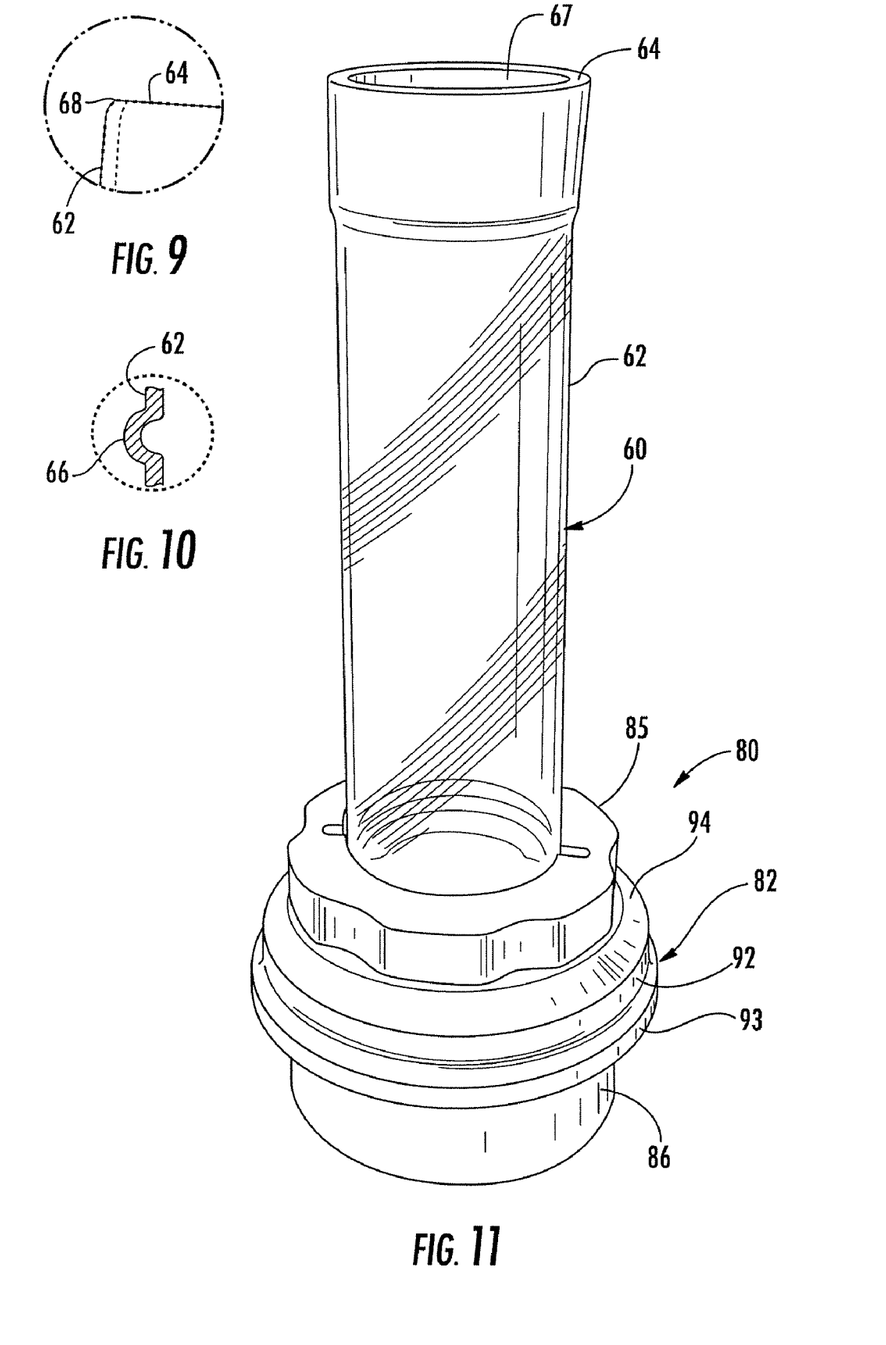
FIG. 9 is an enlarged fragmentary view of the circled area IX of FIG. 6.
FIG. 10 is an enlarged fragmentary cross-sectional view of the circle area X of FIG. 6.
FIG. 11 is an enlarged perspective view of the combustion tube, shown mounted within the lower seal assembly.
Figure 12:
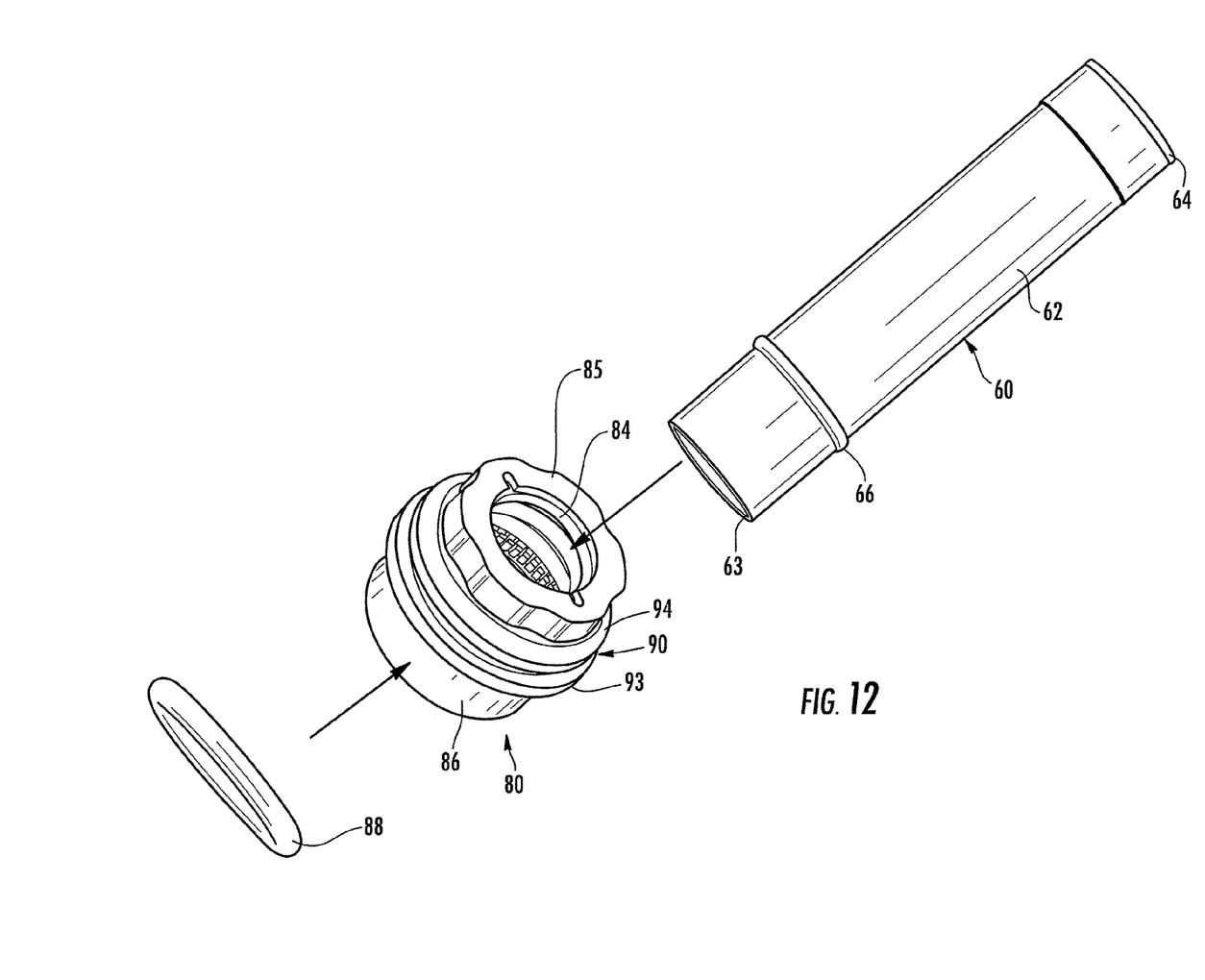
FIG. 12 is an exploded perspective view of the combustion tube and lower seal assembly of the furnace.

The base assembly 80 has a generally cylindrical collar 82 with a central aperture 81 therein for receiving the combustion tube 60, as seen in FIG. 11. Near the upper edge of collar 82 is an annular recess 83 for receiving an O-ring seal 84. A locking cap 85 is threaded onto collar 82 and compresses the O-ring seal once the combustion tube has been inserted therein for sealably holding the combustion tube within the collar 82. Cap 85 engages stop collar 66 of combustion tube 60 compressing seal 84 (FIG. 13) and vertically aligns the combustion tube 60 with respect to the base assembly 80 and ultimately the furnace 20, as seen in FIGS. 2-4 and 13. Collar 82 includes a lower cylindrical sleeve 86 having internal annular recess 87 for receiving a second O-ring 88 for sealing the base assembly 80 onto the lower seal assembly 16 of the furnace. Further, the assembly 80 includes a metal RFI shield 89 and a third sealing O-ring 78 (FIGS. 13 and 15) positioned within an annular recess 91 of collar 82.

Collar 82 includes a cam 90 which has an outer annular vertical surface 92, an upper chamfered surface 94 chamfered upwardly and inwardly at an angle of about 45° from the vertically extending annular surface 92 and a lowered chamfered surface 96 inwardly and downwardly beveled at an angle of about 45° from surface 92. The two surfaces thus form an angle of about 90° between them to fit within a 90° slot 107 (not shown) in the cams 106 and 108. Collar 82 also includes an annular flange 93 having a diameter greater than aperture 59 in furnace housing floor 58 to engage the undersurface of floor 58 when the combustion tube is in an installed locked position as seen in FIG. 3. The cam 90 so-defined interengages with cam pins of cam-actuated assembly 100 for locking and unlocking the combined combustion tube 60 and base assembly 80 as described in greater detail the above identified '628 application.

Figure 13:
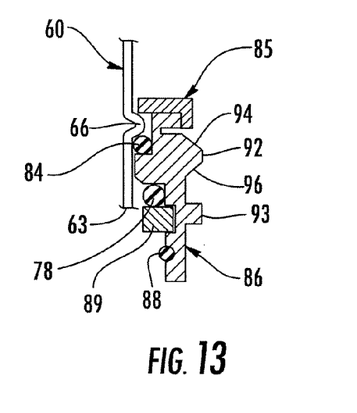
FIG. 13 is an enlarged fragmentary cross-sectional view of the interface between the combustion tube and the lower seal assembly.
Figure 14:
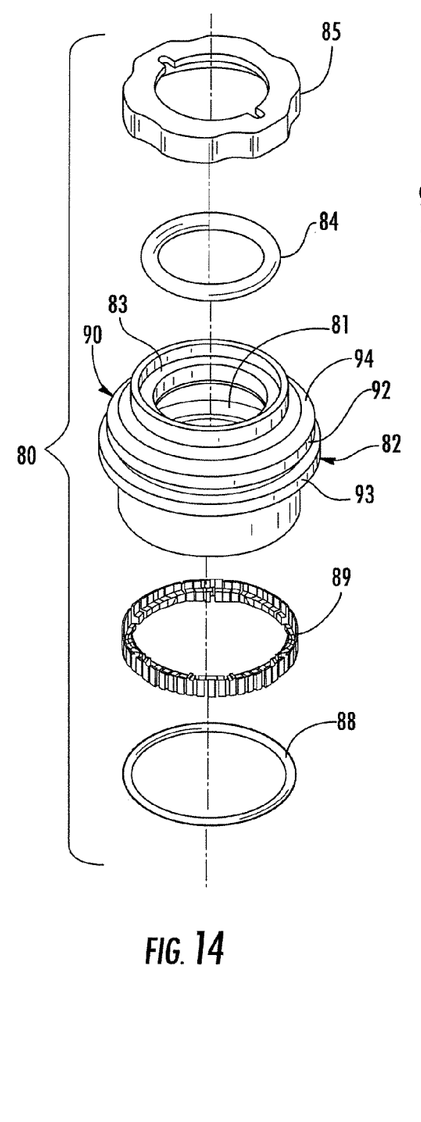
FIG. 14 is an exploded perspective view of the lower seal assembly.
Figure 15:
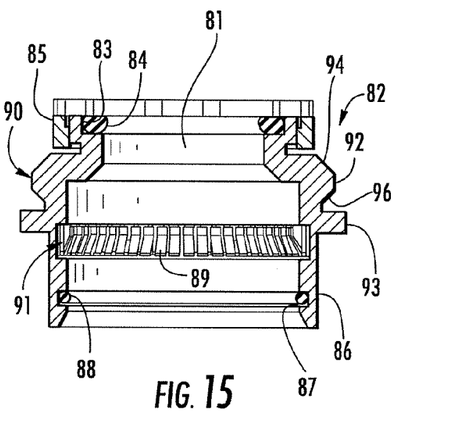
FIG. 15 is an enlarged cross-sectional view of the lower seal assembly.

The combustion tube 60 is made of quartz glass to withstand the temperatures of combustion, which can reach 3000° C. The combustion tube 60 has an overall length (i.e., height) of about 6.12 inches, with the inner diameter D near the top having a diameter of about 1.28 inches. The outer diameter of the cylindrical body 62 of the tube is about 1.48 inches, while the outer stop collar 66 has an outer diameter of about 1.58 inches and a minimum radius of curvature at its intersection with the outer surface 62 of tube 60. The radius of curvature of the collar itself of about 0.010 inches. The vertical height of collar 66 was about 0.157 inches. Thus, the collar 66 projects outwardly from the outer surface 62 of combustion tube 60 about 0.065 inches, a distance sufficient to interface with the base assembly 80 and cap 85 to index and mount the combustion tube to the base assembly 80. The distance to collar 66 from the bottom edge 63 of tube 60 was about 0.83 inches to provide a distance sufficient for the sealed engagement of the lower end 63 of the combustion tube with seal 84, as illustrated in FIG. 13. The wall thickness of tube 60 was, in one preferred embodiment, about 2 mm. Although these dimensions are illustrative of the preferred embodiment of the invention, other sized furnaces may incorporate combustion tubes with proportionally larger or smaller dimensions, as long as the unique mounting and sealing arrangement is provided for the combustion tube. The important feature is that a stop collar is provided in spaced relationship to the lower edge of the combustion tube to allow its indexable and sealable mounting to a base assembly for easy removal, particularly in a furnace having an easily removable combustion tube design.

FIG. 3 illustrates the assembly of the combustion tube 60 to the lower seal assembly 16, which includes an upper ring 65 threadably mounted to the collar 82 of the base assembly. As seen in FIGS. 3, 11 and 13, when combustion tube 60 is inserted into the base assembly 80, the stop collar 66 engages the cylindrical bottom edge of upper ring 85 to precisely position the combustion tube with respect to the base assembly 80. Engaging the bottom of upper ring 85 assures positive removal of the combined assembly 80 and tube 60 when disengaged from furnace 20. This allows assembly 80 to cooperate with the raising and lowering mechanism, including the piston rod 22, lower seal assembly 16, and pedestal 12 (FIGS. 1 and 3) to precisely position the combustion tube 60 within the analytical furnace 20. Thus, with the improved combustion tube of the present invention, an indexing stop is provided to precisely mount and position the combustion tube in the furnace, particularly when used in connection with an easily removable combustion tube mechanism.

It will become apparent to those skilled in the art that various modifications to the preferred embodiment of the invention as described herein can be made without departing from the spirit or scope of the invention as defined by the appended claims.

The invention claimed is:

1. A combustion tube for use in an analytical furnace comprising:
 a generally cylindrical body having open ends allowing the flow of gas through said combustion tube, said body having a tube stop spaced from one end of said body for engaging a combustion tube mounting assembly for positioning the body in a predetermined position with respect to said mounting assembly; and wherein said tube stop is a rounded annular projection extending outwardly from said body.

2. The combustion tube as defined in claim 1 wherein said body has an opposite end with an enlarged inner diameter for receiving an upper seal assembly of a combustion furnace.

3. The combustion tube as defined in claim 2 wherein said opposite end has an outer annular shoulder having a rolled edge to facilitate the insertion of the opposite end through a seal in the upper seal assembly of a furnace.

4. The combustion tube as defined in claim 3 wherein said body is made of quartz glass to withstand combustion temperatures encountered in the furnace.

5. A combustion tube for an induction furnace comprising;
 a generally cylindrical body, said body made of quartz glass, with open ends;
 an integral annular shoulder formed in said body in predetermined spaced relationship to one end of said body and extending outwardly from said body; and
 wherein said body has an opposite end having an increased inner diameter opening.

6. The combustion tube as defined in claim 5 wherein said opposite end has an outer rolled edge.

7. The combustion tube as defined in claim 5 wherein said annular shoulder is rounded in cross section.

8. An analytical furnace comprising:
 an upper seal assembly for receiving an upper end of a combustion tube;
 a combustion tube including a generally cylindrical body and an integral annular shoulder formed in said body in predetermined spaced relationship to a lower end of said body and extending outwardly from said body, and wherein said body has an upper end for mating with said upper seal assembly;
 a lower seal assembly; and
 a mounting assembly having a central opening for receiving said lower end of said combustion tube and a cap, wherein said annular shoulder of said body engages said central opening and said cap for indexably positioning said combustion tube with respect to said lower seal assembly such that, when said furnace is closed, said combustion tube is positioned in predetermined relationship to said furnace and sealed at said upper and lower ends.

9. The furnace as defined in claim 8 wherein said upper end of said body has an enlarged diameter for receiving said upper seal assembly of a combustion furnace.

10. The furnace as defined in claim 9 wherein said upper end of said combustion tube has an outer annular shoulder having a rolled edge to facilitate insertion through a seal in said upper seal assembly of said furnace.

11. The furnace as defined in claim 8 wherein said annular shoulder is rounded in cross section.

12. The furnace as defined in claim 11 wherein said body is made of quartz glass to withstand the temperatures encountered in said furnace.

13. The furnace as defined in claim 12 wherein said furnace is an induction furnace.

14. The furnace as defined in claim 8 wherein said mounting assembly has a base ring and an O-ring and said cap is threadably mounted to said base ring and wherein said annular shoulder is captively held between said base ring and said upper ring and said O-ring.

15. A combustion tube for an induction furnace comprising;
 a generally cylindrical body, said body made of quartz glass, having open ends;
 an integral annular shoulder formed in said body in predetermined spaced relationship of about 0.8 inches from one end of said body and extending outwardly from said body about 0.06 inches; and
 wherein said body has an opposite end having an increased inner diameter opening with a rolled outer edge.

16. The combustion tube as defined in claim 15 wherein said annular shoulder is rounded in cross section and has a radius of curvature of about 0.01 inches.

17. The combustion tube as defined in claim 15 wherein the shape and dimensions of said tube are selected to adapt said tube for use in an induction furnace with an easily removable combustion tube design.

* * * * *